(12) United States Patent
Bonn

(10) Patent No.: US 8,409,187 B2
(45) Date of Patent: Apr. 2, 2013

(54) MICROWAVE ANTENNA PROBE WITH HIGH-STRENGTH CERAMIC COUPLER

(75) Inventor: Kenlyn S. Bonn, Boulder, CO (US)

(73) Assignee: Covidien LP, Mansfield, MA (US)

( * ) Notice: Subject to any disclaimer, the term of this patent is extended or adjusted under 35 U.S.C. 154(b) by 724 days.

(21) Appl. No.: 12/555,576

(22) Filed: Sep. 8, 2009

(65) Prior Publication Data

US 2011/0060325 A1    Mar. 10, 2011

(51) Int. Cl.
*A61B 18/18* (2006.01)
(52) U.S. Cl. ......................................................... 606/33
(58) Field of Classification Search ..................... 606/41, 606/33
See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,572,190 A | 2/1986 | Azam et al. | |
| 4,612,940 A | 9/1986 | Kasevich et al. | |
| 4,798,215 A | 1/1989 | Turner | |
| 4,832,048 A * | 5/1989 | Cohen | 606/41 |
| 5,097,844 A | 3/1992 | Turner | |
| 5,129,396 A | 7/1992 | Rosen et al. | |
| 5,150,717 A * | 9/1992 | Rosen et al. | 607/156 |
| 5,275,597 A | 1/1994 | Higgins et al. | |
| 5,330,518 A | 7/1994 | Neilson et al. | |
| 5,417,210 A | 5/1995 | Funda et al. | |
| 5,916,240 A | 6/1999 | Rudie et al. | |
| 5,938,692 A | 8/1999 | Rudie | |
| 6,031,375 A | 2/2000 | Atalar et al. | |
| 6,047,216 A | 4/2000 | Carl et al. | |
| 6,210,367 B1 | 4/2001 | Carr | |
| 6,223,086 B1 | 4/2001 | Carl et al. | |
| 6,226,553 B1 | 5/2001 | Carl et al. | |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

Esterline Product Literature, "Light Key: Visualize a Virtual Keyboard. One With No Moving Parts", Nov. 1, 2003; 4 pages.

(Continued)

*Primary Examiner* — Michael Peffley
*Assistant Examiner* — Daniel Fowler

(57) ABSTRACT

A microwave antenna probe incorporating a high-strength antenna coupler is described herein. The microwave antenna has a radiating portion connected by a coaxial feedline to a source of therapeutic energy, e.g., a microwave generator. Proximal and distal radiating portions of the antenna assembly are separated by a microwave antenna coupler. In embodiments, the described antenna coupler is generally cylindrical in shape and includes a central section having a diameter substantially equivalent to the radiating sections. The coupler includes end sections of a smaller diameter than the central section that are dimensioned to fit within the ends of the radiating section. The end portions include a groove that is adapted to receive a corresponding rib formed within the respective ends of the radiating section. The coupler includes an axial opening defined therein into which a tubular collar in fixed using an interference fit. The outward forces of the collar and the inward forces of the radiating section places the coupler under compression, which improves the strength of the coupler, and the strength of the overall probe assembly.

18 Claims, 6 Drawing Sheets

U.S. PATENT DOCUMENTS

| | | | |
|---|---|---|---|
| 6,230,060 | B1 | 5/2001 | Mawhinney |
| 6,375,606 | B1 | 4/2002 | Garibaldi et al. |
| 6,496,736 | B1 | 12/2002 | Carl et al. |
| 6,496,738 | B2 | 12/2002 | Carr |
| 6,603,994 | B2 | 8/2003 | Wallace et al. |
| 6,725,080 | B2 | 4/2004 | Melkent et al. |
| 6,878,147 | B2 | 4/2005 | Prakash et al. |
| 6,956,164 | B2 | 10/2005 | Brown |
| 7,128,739 | B2 | 10/2006 | Prakash et al. |
| 7,147,632 | B2 | 12/2006 | Prakash et al. |
| 7,197,363 | B2 | 3/2007 | Prakash et al. |
| 7,311,703 | B2 | 12/2007 | Turovskiy et al. |
| 7,318,824 | B2 | 1/2008 | Prakash et al. |
| 7,439,736 | B2 | 10/2008 | Meaney et al. |
| 7,467,015 | B2 | 12/2008 | Van der Weide |
| 7,565,207 | B2 | 7/2009 | Turner et al. |
| 2002/0022836 | A1 | 2/2002 | Goble et al. |
| 2003/0088242 | A1* | 5/2003 | Prakash et al. .................. 606/33 |
| 2004/0097805 | A1 | 5/2004 | Verard et al. |
| 2004/0242992 | A1 | 12/2004 | Hareyama |
| 2005/0149010 | A1 | 7/2005 | Turovskiy et al. |
| 2006/0264923 | A1 | 11/2006 | Prakash et al. |
| 2006/0282069 | A1 | 12/2006 | Prakash et al. |
| 2006/0293650 | A1 | 12/2006 | Prakash et al. |
| 2007/0233057 | A1 | 10/2007 | Konishi |
| 2007/0270791 | A1* | 11/2007 | Wang et al. ..................... 606/41 |
| 2007/0288079 | A1 | 12/2007 | van der Weide et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 186 274 | 3/2002 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | 03/039385 | 5/2003 |
| WO | WO2004/112628 | 12/2004 |
| WO | 2005/011049 | 2/2005 |
| WO | WO2005/016119 | 2/2005 |

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.

U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With The LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.
Crawford et al., "Use of the LigaSure™ Vessel Sealing System in Urologic Cancer Surger" Grand Rounds In Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College Of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
S. Humphries Jr. et al., "Finite•Element Codes To Model Electrical Heating And Non•Llnear Thermal Transport In Biological Media", Proc. ASME HTD-355, 131 (1997).
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.

European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
US 5,326,343, 07/1994, Rudie et al. (withdrawn)

* cited by examiner

MICROWAVE ANTENNA PROBE WITH HIGH-STRENGTH CERAMIC COUPLER

BACKGROUND

1. Technical Field

The present disclosure relates to systems and methods for providing energy to biological tissue and, more particularly, to a microwave ablation surgical probe having a high strength ceramic puck assembly, and methods of use and manufacture therefor.

2. Background of Related Art

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such microwave ablation procedures are typically performed to ablate and coagulate targeted tissue to denature or kill the tissue. Many procedures and types of devices utilizing electromagnetic radiation therapy are known in the art. Such microwave therapy is typically used in the treatment of tissue and organs such as the prostate, heart, and liver.

Presently, there are several types of microwave probes in use, e.g., monopole, dipole, and helical. A monopole antenna probe consists of a single, elongated microwave conductor exposed at the end of the probe. The probe is typically surrounded by a dielectric sleeve. A dipole antenna consists of a coaxial construction having an inner conductor and an outer conductor with a dielectric junction separating a portion of the inner conductor, which may be coupled to a portion corresponding to a first dipole radiating section, and a portion of the outer conductor which may be coupled to a second dipole radiating section. The dipole radiating sections may be configured such that one radiating section is located proximally of the dielectric junction, and the other portion is located distally of the dielectric junction. In both the monopole and dipole antenna probe, microwave energy generally radiates perpendicularly from the axis of the conductor.

The typical microwave probe has a long, thin inner conductor which extends along the axis of the probe and is surrounded by a dielectric material and is further surrounded by an outer conductor around the dielectric material such that the outer conductor also extends along the axis of the probe. In another variation of the probe, which provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or a combination thereof.

Invasive procedures have been developed in which a microwave antenna probe may be either inserted directly into a point of treatment via a normal body orifice, or inserted percutaneously. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed.

Structurally rigid invasive probes exist, and are typically long, narrow, needle-like antenna probes which may be inserted directly into the body tissue to directly access a site of a tumor or other malignancy. Such rigid probes generally have small diameters that aid not only in ease of use but also reduce the resulting trauma to the patient. A convenience of rigid antenna probes, that are capable of direct insertion into tissue, is that such probes may also allow for alternate additional uses in different situations. However, a dielectric junction, or puck, that separates radiating sections of a rigid probe, may be subjected to bending, compression, and rotational forces during manufacture, and during use. Such forces may lead to failure of the puck, causing mechanical or electrical failure of the probe. This effect may be exacerbated by the structural properties of suitable dielectric materials, such as porcelain or other ceramic materials, which tend to be brittle.

SUMMARY

The present disclosure provides a high-strength microwave antenna coupler assembly, or puck, and methods of manufacture thereof. In some variations, the microwave antenna assembly has proximal and distal radiating portions. The puck assembly may be a junction member that couples the proximal and distal radiation sections. At least a portion of the coupler assembly may be disposed between the proximal and distal radiating sections. The distal end of the distal radiating section may have a tapered end which terminates at a tip configured to allow for the direct insertion into tissue with minimal resistance. A coaxial feedline having an inner and an outer conductor may extend through the proximal radiating section, having the inner conductor disposed within the outer conductor and having a dielectric (e.g., insulator) disposed therebetween. The inner conductor may extend through an opening or channel disposed longitudinally through the coupler assembly. The inner conductor may further extend at least partially into the distal radiating section. The microwave antenna assembly may also be connected to a source of microwave energy.

The puck includes a high strength ceramic stepped cylindrical body having one or more stepped portions on an outer surface thereof and an axial channel formed therethrough. The axial channel accommodates at least a portion of the feedline, e.g., the inner conductor, to provide microwave energy to the distal radiating section. The stepped cylindrical body may be formed from high-strength ceramic material, such as without limitation, Zirconia, or Alumina Zirconia composite. The stepped cylindrical body includes a proximal section, a center section, and a distal section. In an embodiment, the proximal section and the distal section have similar external diameters, while the center section has a greater diameter than that of either the proximal or distal section. The outer diameter of the center section may be substantially equal to the outer diameter of the proximal radiating section and the distal radiating section, to provide a consistent probe outer diameter. The proximal section and distal section of the stepped cylindrical body include a circumferential groove defined therein dimensioned to mate with a corresponding circumferential ridge disposed within an inner surface of a distal end of the proximal radiating section, and within a proximal end of the distal radiating section, respectively. A collar may be fitted within the axial channel. The collar may be formed from metallic material. The collar may be fitted into the axial opening by interference fit, e.g., press fit or friction fit. The collar may provide outward radial tension to the puck which, when combined with the inward tensile forces applied to the puck by the radiating sections, preloads the puck compressively, thereby greatly increasing the strength of the ceramic puck body and/or the microwave probe assembly.

In an embodiment, a microwave antenna coupler in accordance with the present disclosure includes a generally cylindrical body, or puck. The cylindrical body may be formed from ceramic material as described hereinabove. The body may have a central portion having a first diameter, and an end portion having a second diameter that is less than the first diameter. The body may have two end portions wherein one end portion is proximal to the central portion, and another end portion is distal to the central portion. A groove is circumferentially disposed upon an outer surface of the end portion, having a third diameter that is less than the second diameter. The groove is adapted to receive a corresponding rib that is disposed on an inner surface of a radiating section. The body includes an axial opening disposed through the body. The axial opening may extend from a proximal end of the body to a distal end of the body. A tubular collar may be fixed within the axial opening.

The present disclosure is also directed to a method of manufacturing a microwave antenna coupler that includes the steps of forming a high strength ceramic stepped cylindrical puck having one or more stepped portions on an outer surface thereof and an axial opening formed therethrough, which may formed by molding and/or machining, and inserting a tubular collar within the axial opening. The tubular collar may be fixed within the axial opening by interference fit.

Also disclosed is a method of manufacturing a microwave antenna probe that includes the steps of providing a microwave antenna coupler comprising a cylindrical body having a central portion having a first diameter, and an end portion having a second diameter that is less than the first diameter. An outer surface of the end portion includes a groove circumferentially disposed thereupon, the groove having a third diameter that is less than the second diameter. The groove is adapted to receive a corresponding rib disposed on an inner surface of a radiating section. The cylindrical body includes an axial opening disposed through the body having a tubular collar dimensioned to interference fit within the axial opening. The tubular collar is press-fitted into the axial opening. At least two semicylindrical radiating subsections are provided, each having a rib disposed on a respective inner surface thereof that is dimensioned to engage the groove. The semicylindrical radiating subsections are positioned over end portion such that the rib engages the groove. The semicylindrical radiating subsections are joined to form a radiating section.

Alternatively, a fully cylindrical radiating subsection may be provided that includes an internal rib formed by any suitable means, e.g., machine or molding. The fully cylindrical radiating subsection may then be thermally expanded during manufacture to facilitate alignment of the rib and groove, then cooled to fit.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
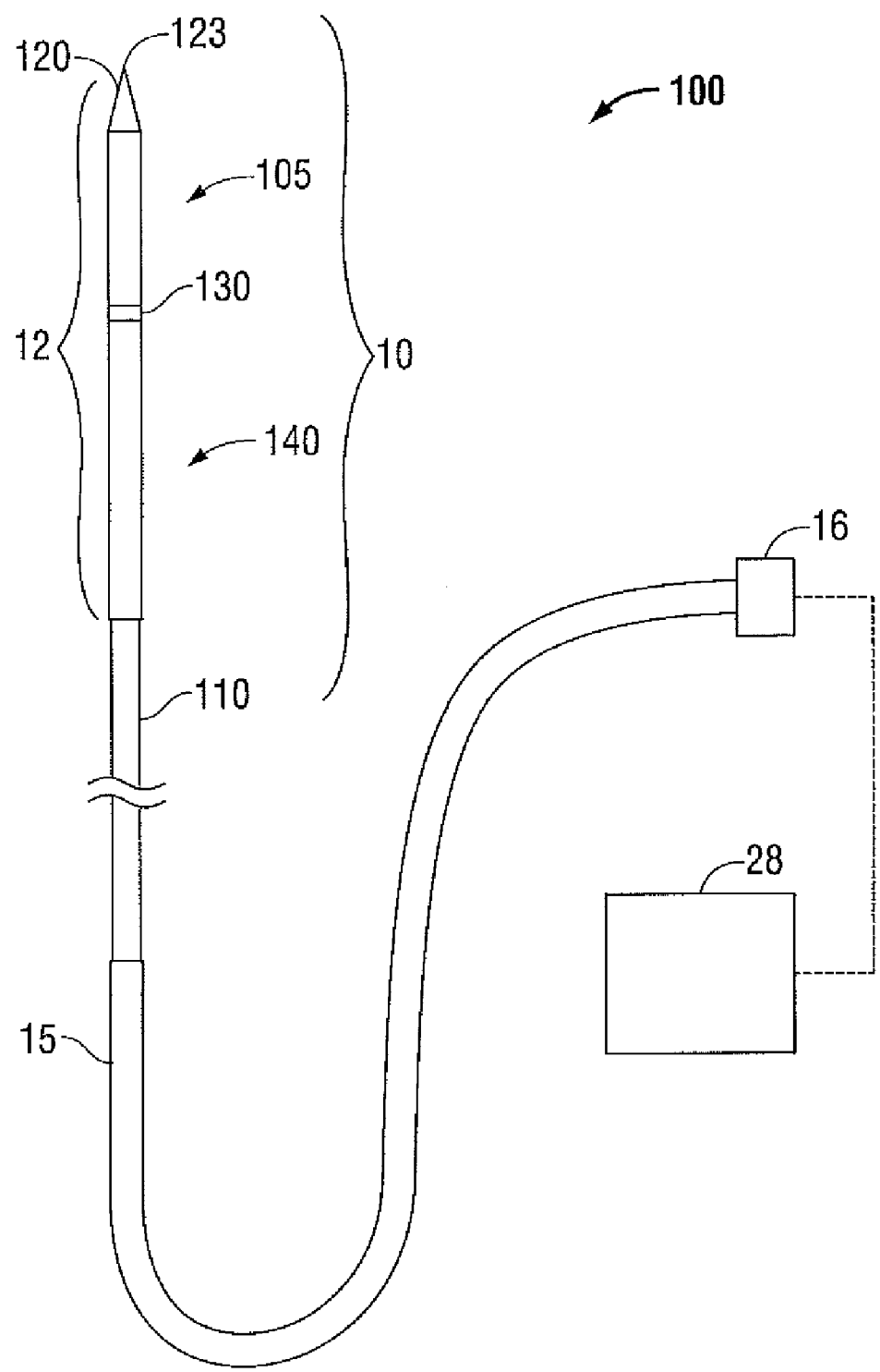
FIG. 1 shows a representative diagram of a microwave antenna assembly in accordance with the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

FIG. 1 shows an example embodiment of a microwave ablation system 100 in accordance with the present disclosure. The microwave ablation system 100 includes an antenna probe assembly 10 having a radiating portion 12 that is connected by coaxial feedline 110 via cable 15 to connector 16, which may further connect the probe 10 to a power generating source 28, e.g., a microwave generator. Probe assembly 10, as shown, is a dipole microwave antenna probe assembly, but other antenna assemblies, e.g., monopole or leaky wave antenna assemblies, may also utilize the principles set forth herein. Distal radiating portion 105 of radiating portion 12 may have a tapered end 120 which terminates at a tip 123 to allow for insertion into tissue with minimal resistance. Alternatively, tip 123 may be rounded or flat. Proximal radiating portion 140 is joined to distal radiating portion 105 by puck assembly 130.

Figure 2:
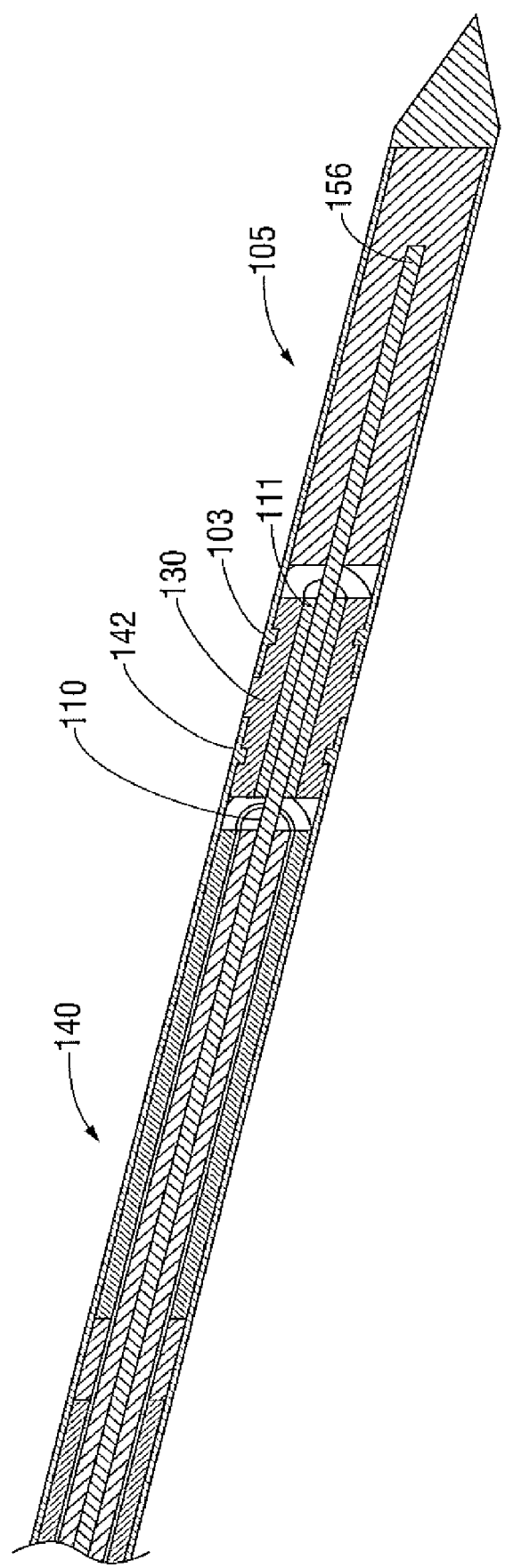
FIG. 2 shows a perspective, cross-sectional view of an embodiment of a microwave antenna assembly in accordance with the present disclosure.
Figure 3:
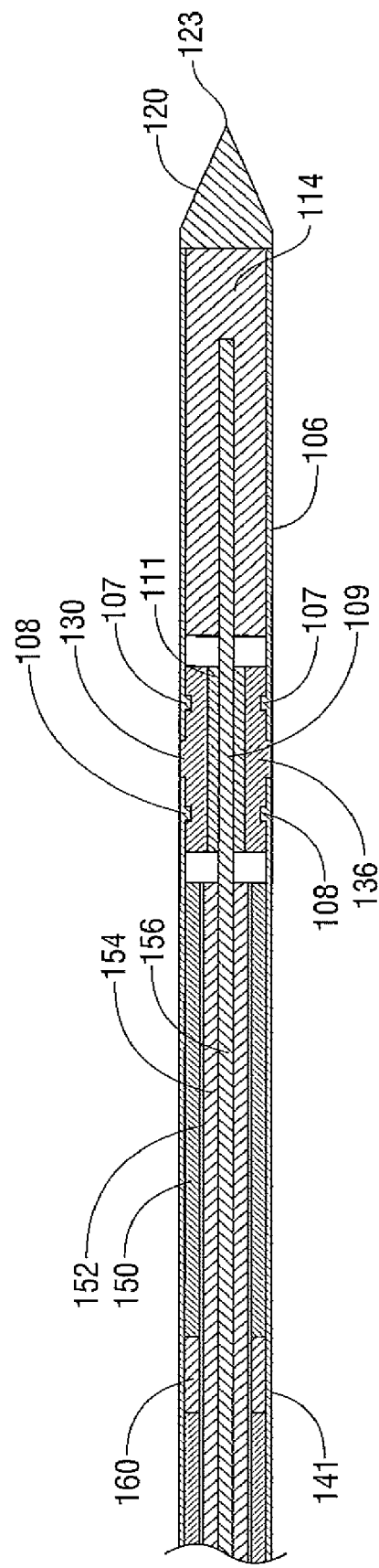
FIG. 3 shows a side, cross-sectional view of an embodiment of a microwave antenna assembly in accordance with the present disclosure.

With reference generally to FIGS. 2-3, a high-strength microwave antenna puck assembly 130 is presented in accordance with the present disclosure. Puck assembly 130 includes a body 136 having a generally stepped cylindrical shape characterized by a proximal section 133 and a distal section 132, and having a center section 131 therebetween. Proximal section 133 and distal section 132 may have a substantially equal outer diameter. The outer diameter of center section 131 is greater than the outer diameter of proximal section 133 and/or distal section 132. Body 136 may be formed from high-strength ceramic material, for example without limitation, Zircona and/or Alumina ceramic compound. Body 136 may be formed from material having electrically non- or low-conductive properties (e.g., dielectric material).

Figure 4:
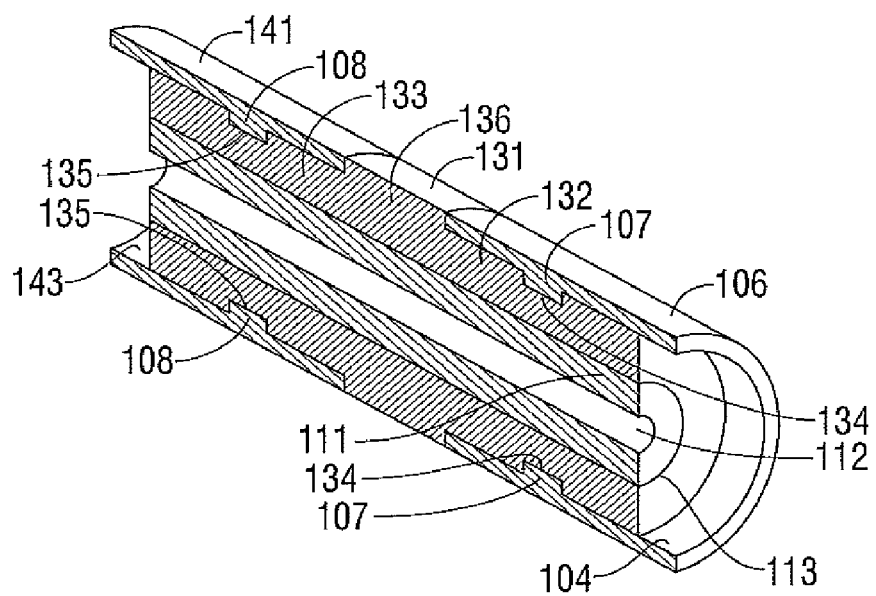
FIG. 4 shows a perspective, cross-sectional view of an embodiment of a puck assembly in accordance with the present disclosure.
Figure 5:
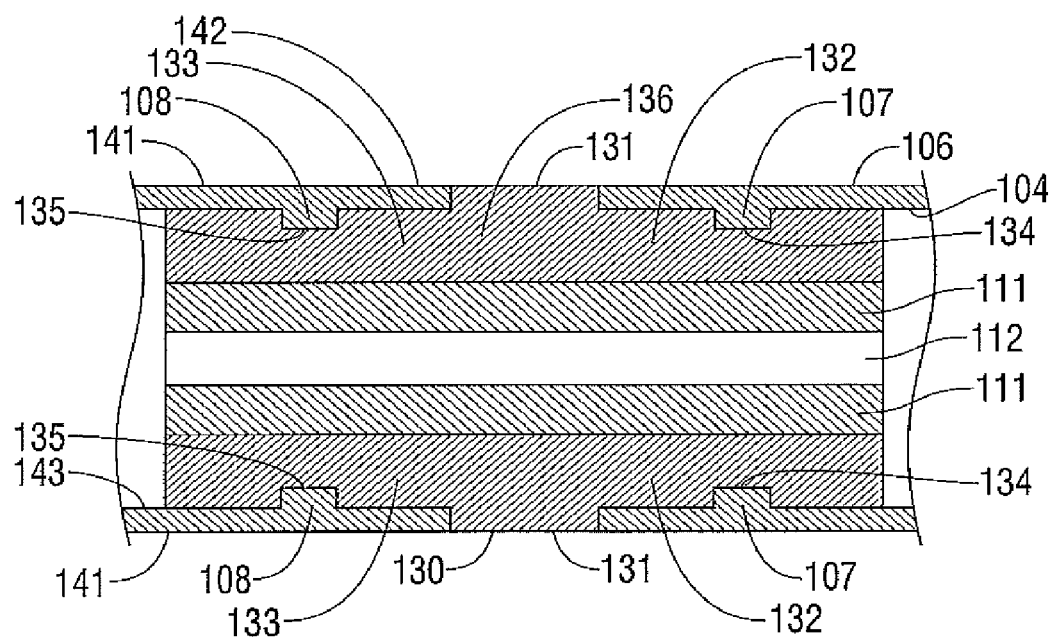
FIG. 5 shows a side, cross-sectional view of an embodiment of a puck assembly in accordance with the present disclosure.

With particular reference to FIGS. 4 and 5, body 136 includes an opening 113 defined axially therethough having a circular cross-section. Opening 113 is dimensioned to receive a collar 111 having a generally tubular shape and having a passage 112 formed therethough. Collar 111 may be formed from metallic material, such as without limitation, stainless steel, copper, aluminum, or any heat-resistant metal or alloy. Collar 111 may be fixed within opening 113 by any suitable means, such as without limitation, interference fit (e.g., press-fit or friction fit). Additionally or alternatively, collar 111 may be integrally formed with inner conductor 156. Collar 111 may impart outward radial force to body 136 which may place body 136 in compression in cooperation with radiating sections 106 and 141, as will be described in further detail below.

As seen in FIG. 1, radiating portion 12 includes proximal radiating portion 140 and distal radiating portion 105. An outer surface of proximal radiating portion 140 is formed from proximal radiating section 141. An outer surface of distal radiating portion 105 is formed from distal radiating section 106. Radiating sections 141 and 106 may be formed from any suitable heat-resistant metallic material, such as without limitation, stainless steel. Distal radiating section 106 is coupled to tapered end 120 having a tip 123 that is contoured to facilitate the insertion of probe 10 into tissue. Tapered end 120 and/or tip 123 may be integrally formed with distal radiating section 106. Radiating sections 141 and 106 may be formed by joining semicylindrical subsections thereof e.g., by joining two or more "clamshell" sections, which facilitates the engagement of the ribbed inner surfaces of the radiating sections with the grooved outer surfaces of the puck ends, as will be described in detail hereinbelow.

A coaxial feedline 110 extends from a proximal end of the probe 10, which may include a handle (not explicitly shown), wherein the coaxial feedline 110 is adapted to provide radiofrequency and/or microwave ablation energy to the probe 10 generally, and more specifically, to proximal radiating portion 140 and distal radiating portion 105. Coaxial feedline 110 may exhibit an impedance of 50Ω. Coaxial feedline 110 includes, in coaxial arrangement, an insulating outer sheath 150, an outer coaxial conductor 152 coaxially disposed within outer sheath 150, a dielectric layer 154 coaxially disposed within coaxial conductor 152, and an inner conductor 156 coaxially disposed within dielectric layer 154. As seen in FIG. 3, a ring-like balun 160 may disposed in electrical communication between outer conductor 152 and proximal radiation section 141 to control the delivery of radiofrequency and/or microwave energy into tissue (e.g., the ablation pattern) of probe 10. Inner conductor 156 of coaxial feedline 110 passes through channel 112 of interference collar 111. Inner conductor 156 may additionally be joined to interference collar 112 by, e.g., soldering, brazing, or laser welding. In an embodiment, the inner conductor 156 may place the body 136 under lateral tension with proximal radiating section 141 and/or distal radiating section 116, which may improve the overall strength and rigidity of the probe 10. Inner conductor 156 may additionally or alternatively be coupled in electrical communication to distal radiating section support 114.

Proximal radiating portion 140 and distal radiation portion 105 are joined by puck assembly 130. A distal end 142 of proximal radiating section 141 is coupled to puck proximal section 133. A proximal end 103 distal radiating section 106 is coupled to puck distal section 132. As best seen in FIGS. 4, 5, and 7A-B, puck proximal section 133 includes a circumferential groove 135 disposed on an outer surface thereof that is dimensioned to engage a corresponding rib 108 formed on an inner surface 143 of proximal radiating section 141. Puck distal section 132 includes a circumferential groove 134 that is dimensioned to engage a corresponding rib 107 formed on an inner surface 104 of distal radiating section 106. Groove 134, 135 may be formed by any suitable manner of fabrication, including without limitation machining, laser etching, chemical etching, molding, and or forging. Rib 107, 108 may be formed by any suitable manner of fabrication, including without limitation machining, brazing, molding, and/or forging.

Figure 6:
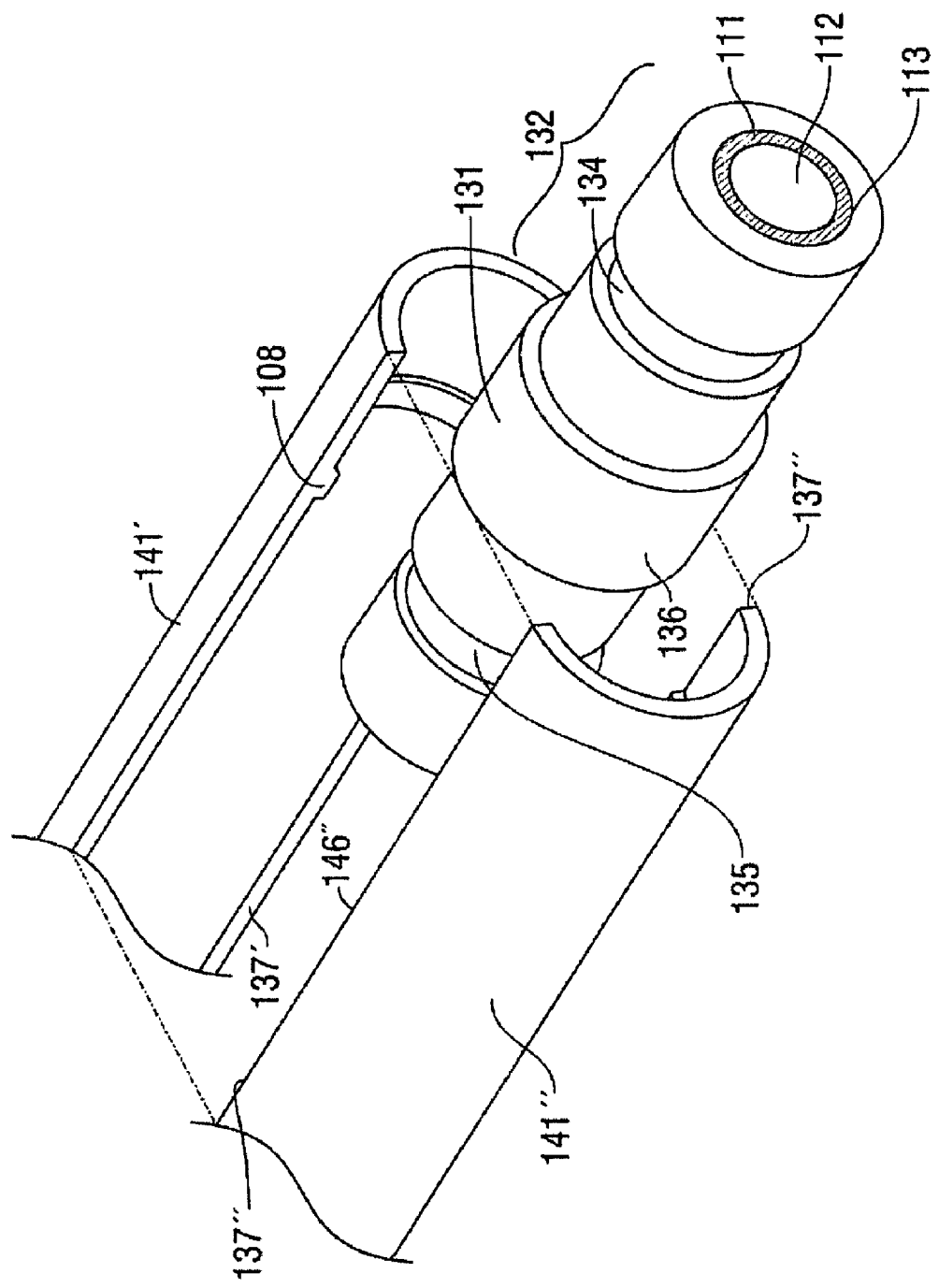
FIG. 6 shows a perspective view of an embodiment of a puck assembly in accordance with the present disclosure.
Figure 7A:
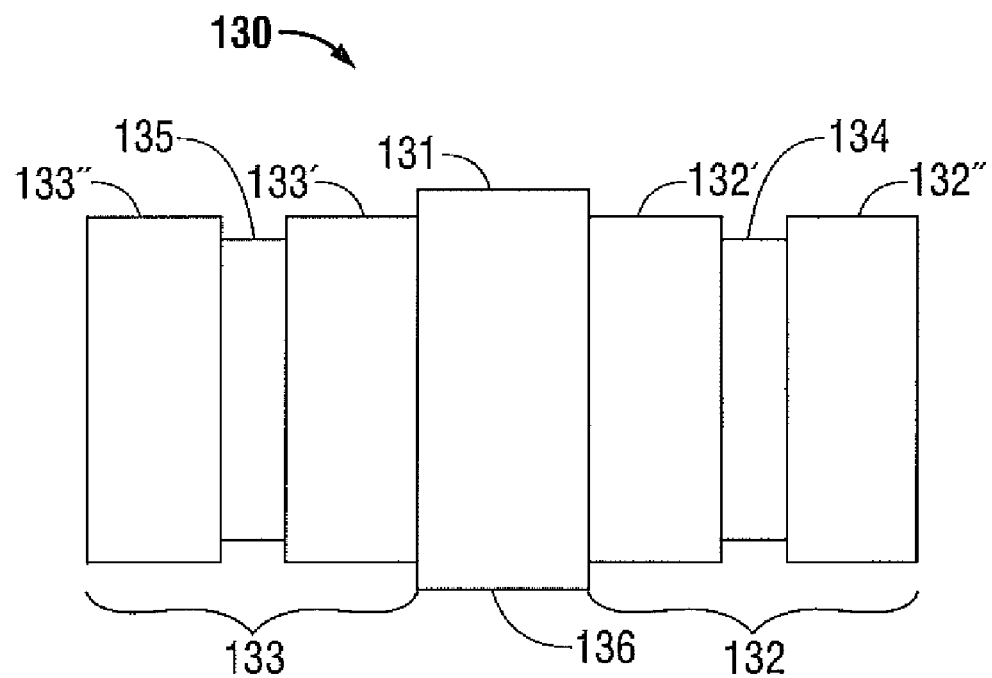
FIG. 7A shows a side, elevation view of an embodiment of a puck assembly in accordance with the present disclosure.
Figure 7B:
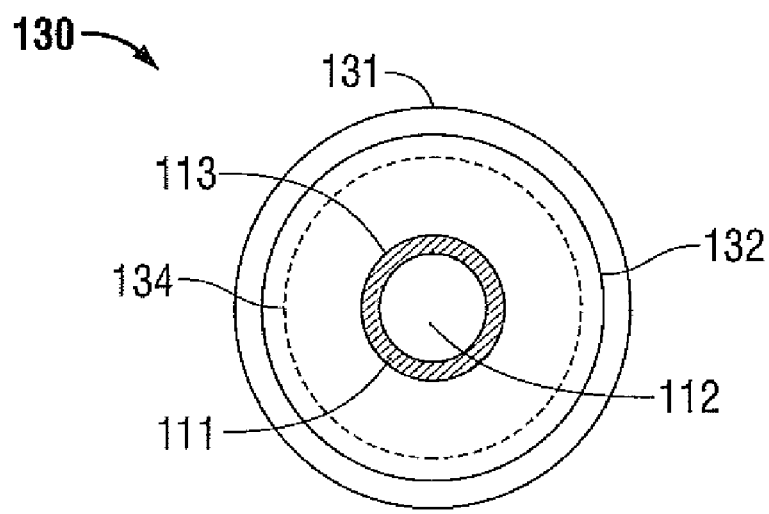
FIG. 7B shows an end, elevation view of an embodiment of a puck assembly in accordance with the present disclosure.

As best illustrated in FIG. 6, proximal radiating section 141 may be formed from two semicylindrical subsections 141' and 141" (e.g., "clamshells"). In one envisioned manner of manufacture, the halves 141' and 141" are brought together over puck proximal section 133 whereby rib 108 engages groove 135. Compression is applied to halves 141' and 141". Edges 137', 137" thereof are joined by any suitable manner of attachment, including without limitation soldering, brazing, adhesive bonding, or welding, thereby placing at least a portion of puck body 136 under constant compression. Distal radiating section 106 may also be formed from two semicylinddical halves (not explicitly shown) and joined to puck distal section 132 in the manner previously described, e.g., by bringing together the semicylindrical halves of the distal radiating section over the puck distal portion under compression wherein rib 107 engages groove 134, and joining the distal radiating section halves (not explicitly shown) along a common edge 137', 137" thereof by, e.g., brazing or laser welding as previously described herein.

In an embodiment, puck proximal section 133 and/or puck distal section 132 may include a metallization layer (not explicitly shown) disposed on at least a part of an outer surface thereof, e.g., groove 135, groove 135, surface 133', 133", 132', and/or 132". The metallization layer may be deposited on puck by any suitable manner, such as without limitation sputtering, electroplating, vacuum deposition, chemical vapor deposition, or arc vaporization. The proximal radiating section halves 141', 141" and/or the distal radiating section halves (not explicitly shown) may then be brazed and/or soldered to the metalized surfaces of puck body 136. Additionally or alternatively, the radiating halves may be joined (by e.g., brazing, soldering, laser welding, or the like) along a common edge 137', 137" thereof as previously described herein. The puck assembly 130 and/or probe 12 may be strengthened by bonding the radiating sections 116, 141 to the metalized surfaces of the puck body 136 in the described manner, and may better resist rotational moments between the radiating sections 116, 141 and puck assembly 130.

An outer surface of the probe 10, e.g., an outer surface of puck center section 131, proximal radiating section 141, distal radiating section 106, and/or tip 120, may include a lubricious coating (not explicitly shown). The lubricious coating may be formed from any suitable low friction material having the ability to withstand the operating temperature of the probe, such as without limitation, polytetrafluoroethylene (a.k.a. PTFE or Teflon®, manufactured by the E.I. du Pont de Nemours and Co. of Wilmington, Del., USA), polyethylene tephthalate (PET), or the like. Additionally or alternatively, an outer surface of the probe 10 as previously described may include a heat shrink covering, such as polyolefin tubing, or any suitable heat-shrink material.

A method of manufacturing a microwave antenna probe in accordance with the present disclosure includes the steps of providing a microwave antenna coupler 130 comprising a generally cylindrical body 136 having a central portion 131 having a first diameter, and at least one end portion 132, 133 having a second diameter that is less than the first diameter. An outer surface 132', 132" and/or 133', 133" of an end portion 132, 133 includes a groove 134, 135 circumferentially disposed thereupon, the groove having a third diameter that is less than the second diameter. The groove 134, 135 is adapted to receive a corresponding rib 107, 108 disposed on an inner surface of a distal radiating section 106 and/or proximal radiating section 141, respectively. The cylindrical body 136 includes an axial opening 113 disposed through the body 136 having a tubular collar 111 dimensioned to interference fit within the axial opening 113. The tubular collar 111 is press-fitted into the axial opening 113. At least two semicylindrical proximal radiating subsections 141', 141" are provided, each having a rib 108 disposed on a respective inner surface 143 thereof that is dimensioned to engage the groove 135. At least two semicylindrical distal radiating subsections (not explicitly shown) are provided, each having a rib 107 disposed on a respective inner surface 104 thereof that is dimensioned to engage the groove 134. The semicylindrical radiating subsections are positioned over the respective end portion 133, 132 thereof such that the rib 108 engages the groove 135 and the rib 107 engages the groove 134. The semicylindrical radiating subsections are joined to form a radiating section using, for example without limitation, soldering, brazing, adhesive, or welding.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A microwave antenna coupler, comprising:
    a cylindrical body that includes:
        a central portion having a first diameter;
        an end portion having a second diameter that is less than the first diameter;
        a groove circumferentially defined within an outer surface of the end portion having a third diameter that is less than the second diameter and adapted to receive a corresponding rib disposed on an inner surface of a radiating section;
        an axial opening disposed through the body; and
    a tubular collar fixed within the axial opening, wherein the tubular collar is formed from metallic material.

2. The microwave antenna coupler according to claim 1, wherein the tubular collar is fixed within the axial opening by an interference fit.

3. The microwave antenna coupler according to claim 1, wherein the body is formed from ceramic material.

4. The microwave antenna coupler according to claim 3, wherein the ceramic material is selected from the group consisting of Zirconia, and an Alumina Zirconia composite.

5. The microwave antenna coupler according to claim 4, wherein an outer surface of the end portion includes a metallization layer.

6. The microwave antenna coupler according to claim 1, wherein the body includes at least two end portions.

7. The microwave antenna assembly of claim 6, wherein the body includes a first end portion extending proximally of the central portion and a second end portion extending distally of the central portion.

8. The microwave antenna assembly of claim 7, further comprising a first radiating section having a distal end joined to the first end portion of the body, and a second radiating section having a proximal end joined to the second end portion of the body.

9. The microwave antenna assembly of claim 6, wherein the tubular collar is fixed within the axial opening by interference fit.

10. A microwave antenna assembly for applying microwave energy therapy comprising:
    a coupling assembly, comprising:
        a cylindrical body that includes:
            a central portion having a first diameter;
            an end portion having a second diameter that is less than the first diameter;
            a groove circumferentially defined within an outer surface of the end portion having a third diameter that is less than the second diameter and adapted to receive a rib circumferentially disposed on an inner surface of a radiating section;
            an axial opening disposed through the body; and
        a tubular collar fixed within the axial opening, wherein the tubular collar is formed from metallic material; and
    a radiating section, having a rib circumferentially disposed on an inner surface thereof, and fixed to the coupler wherein the rib engages the groove.

11. The microwave antenna assembly of claim 10, wherein an outer diameter of the radiating section is substantially equal to an outer diameter of the central portion of the cylindrical body.

12. The microwave antenna assembly of claim 10, wherein an inner diameter of the radiating section is substantially equal to an outer diameter of the end portion of the cylindrical body.

13. The microwave antenna assembly of claim 10, wherein the radiating portion is substantially tubular.

14. The microwave antenna assembly of claim 10, wherein the radiating portion is formed from metallic material.

15. The microwave antenna assembly of claim 14, wherein the metallic material includes stainless steel.

16. The microwave antenna assembly of claim 10, wherein an outer surface of the microwave antenna assembly includes a lubricious coating.

17. The microwave antenna assembly of claim 10, wherein an outer surface of the microwave antenna assembly includes a heat shrink covering.

18. The microwave antenna assembly of claim 10, further comprising a coaxial feedline having an inner conductor disposed within an outer conductor and having a dielectric therebetween, wherein at least a part of the inner conductor extends distally through the tubular collar.

* * * * *